(12) United States Patent
Lucente-Schultz et al.

(10) Patent No.: US 10,435,616 B2
(45) Date of Patent: Oct. 8, 2019

(54) CATIONIC AMMONIUM SURFACTANTS AS LOW DOSAGE HYDRATE INHIBITORS

(71) Applicant: Ecolab USA Inc., St. Paul, MN (US)

(72) Inventors: Rebecca Michele Lucente-Schultz, Missouri City, TX (US); Jeff Servesko, Sugar Land, TX (US)

(73) Assignee: Ecolab USA Inc., St. Paul, MN (US)

( * ) Notice: Subject to any disclaimer, the term of this patent is extended or adjusted under 35 U.S.C. 154(b) by 212 days.

(21) Appl. No.: 15/522,906

(22) PCT Filed: Oct. 30, 2015

(86) PCT No.: PCT/US2015/058216
§ 371 (c)(1),
(2) Date: Apr. 28, 2017

(87) PCT Pub. No.: WO2016/069987
PCT Pub. Date: May 6, 2016

(65) Prior Publication Data
US 2017/0335169 A1 Nov. 23, 2017

Related U.S. Application Data

(63) Continuation-in-part of application No. 14/528,877, filed on Oct. 30, 2014, now Pat. No. 9,765,254.

(51) Int. Cl.
*C09K 8/52* (2006.01)
*C07C 237/06* (2006.01)
*C07C 237/10* (2006.01)

(52) U.S. Cl.
CPC .............. *C09K 8/52* (2013.01); *C07C 237/06* (2013.01); *C07C 237/10* (2013.01); *C09K 2208/22* (2013.01)

(58) Field of Classification Search
CPC . C07C 237/06; C07C 237/10; C09K 2208/22; C09K 8/52
See application file for complete search history.

(56) References Cited

U.S. PATENT DOCUMENTS

| | | | |
|---|---|---|---|
| 4,022,606 A | 5/1977 | Conrad et al. | |
| 6,566,309 B1 | 5/2003 | Klug et al. | |
| 7,264,653 B2 | 9/2007 | Panchalingam et al. | |
| 7,381,689 B2 | 6/2008 | Panchalingam et al. | |
| 8,618,025 B2 | 12/2013 | Webber | |
| 2005/0081432 A1 | 4/2005 | Panchalingam et al. | |
| 2012/0078021 A1 | 3/2012 | Durham et al. | |
| 2012/0157351 A1 | 6/2012 | Webber | |
| 2012/0161070 A1 | 6/2012 | Webber et al. | |
| 2014/0066683 A1 | 3/2014 | O'Rear et al. | |
| 2016/0122619 A1 | 5/2016 | Lucente-Schultz et al. | |

FOREIGN PATENT DOCUMENTS

| | | |
|---|---|---|
| GB | 2349889 A | 11/2000 |
| JP | 2013-28672 A | 2/2013 |
| WO | 2010/045523 A1 | 4/2010 |
| WO | 2013/032756 A1 | 3/2013 |
| WO | 2013089802 A1 | 6/2013 |

OTHER PUBLICATIONS

International Search Report and Written Opinion issued for PCT/US2015/058216 dated Jan. 27, 2016, 13 pages.
Kelland, M. A., et al., "Studies on Some Alkylamide Surfactant Gas Hydrate Anti-Agglomerants," Chemical Engineering Science, 2006, pp. 4290-4298, vol. 61.
International Search Report and Written Opinion dated Jul. 17, 2016 relating to PCT Application No. PCT/US2016/025257, 16 pages.
Karaaslan, Ugur et al., Effect of Surfactants on Hydrate Formation Rate, Annals New York Academy of Sciences, pp. 735-743 (Date Unknown).
Mady, Mohamed F. et al., The first kinetic hydrate inhibition investigation on fluorinated polymers: Poly (fluoroalkylacrylamide)s, Chemical Engineering Science 119 (2014), pp. 230-235.
Murshed, M. Mangir et al., The role of hydrochlorofluorocarbon densifiers in the formation of clathrate hydrates in deep boreholes and subglacial environments, Annals of Glaciology 47 (2007) pp. 109-114.
Yoslim, Jeffry et al., Enhanced growth of methane-propane clathrate hydrate crystals with sodium dodecyl sulfate, sodium tetradecyl sulfate, and sodium hexadecyl sulfate surfactants, Journal of Crystal Growth 313 (2010) pp. 68-80.

*Primary Examiner* — Alicia Bland
(74) *Attorney, Agent, or Firm* — Stinson LLP

(57) ABSTRACT

This disclosure relates to anti-agglomerant low dosage hydrate inhibitors that can inhibit the formation of hydrate agglomerants and/or plugs. The anti-agglomerant low dosage hydrate inhibitors can be surfactants. The hydrate inhibitors can be used for inhibiting, retarding, mitigating, reducing, controlling and/or delaying formation of hydrocarbon hydrates, agglomerants of hydrates, and/or plugs. The hydrate inhibitors can be applied to prevent, reduce, and/or mitigate plugging of conduits, pipes, transfer lines, valves, and other places or equipment where hydrocarbon hydrate solids can form. The hydrate inhibitors can be zwitterionic or cationic ammonium surfactants.

16 Claims, No Drawings

CATIONIC AMMONIUM SURFACTANTS AS LOW DOSAGE HYDRATE INHIBITORS

CROSS-REFERENCE TO RELATED APPLICATIONS

This application claims priority to PCT Patent Application No. PCT/US2015/058216 filed Oct. 30, 2015, which claims priority to U.S. Continuation-in-Part patent application Ser. No. 14/528,877 filed on Oct. 30, 2014, the disclosure of which is incorporated herein by reference in its entirety.

BACKGROUND

1. Field of the Invention

This disclosure relates generally to compositions and methods for reducing or inhibiting the growth, formation, and/or agglomeration of hydrate particles in fluids. More specifically, the disclosure relates to zwitterionic and cationic ammonium surfactants used for reducing or inhibiting hydrate agglomeration in the production and transport of petroleum fluids, whereas a petroleum fluid is defined as a mixture of varying amounts of water/brine, crude oil/condensate, and natural gas.

2. Description of the Related Art

Since Hammerschmidt discovered in 1934 that gas hydrates could block gas pipelines, research for the prevention of hydrate formation and agglomeration has become increasingly popular. Gas hydrates can easily form during the transportation of oil and gas in pipelines when the appropriate conditions are present. Water content, low temperatures, and elevated pressure are generally required for the formation of gas hydrates. The formation of gas hydrates often results in lost oil production, pipeline damage, and safety hazards to field workers. Modern oil and gas technologies commonly operate under severe conditions during the course of oil recovery and production, such as high pumping speed, high pressure in the pipelines, extended length of pipelines, and low temperature of the oil and gas flowing through the pipelines. These conditions are particularly favorable for the formation of gas hydrates, which can be particularly hazardous for oil productions offshore or for locations with cold climates.

Gas hydrates are ice-like solids that are formed from small, nonpolar molecules and water at lower temperatures and at increased pressures. Under these conditions, the water molecules can form cage-like structures around these small nonpolar molecules (typically dissolved gases such as carbon dioxide, hydrogen sulfide, methane, ethane, propane, butane and iso-butane), creating a type of host-guest interaction also known as a clathrate or clathrate hydrate. The specific architecture of this cage structure can be one of several types (called type 1, type 2, type H), depending on the identity of the guest molecules. However, once formed, these crystalline cage structures tend to settle out from the solution and accumulate into large solid masses that can travel by oil and gas transporting pipelines, and potentially block or damage the pipelines and/or related equipment. The damage resulting from a blockage can be very costly from an equipment repair standpoint, as well as from the loss of production, and finally the resultant environmental impact.

The industry uses a number of methods to prevent these blockages, such as thermodynamic hydrate inhibitors (THI), anti-agglomerant hydrate inhibitors (AAs), and kinetic hydrate inhibitors (KHIs). The amount of chemical needed to prevent blockages varies widely depending upon the type of inhibitor employed. Thermodynamic hydrate inhibitors are substances that can reduce the temperature at which the hydrates form at a given pressure and water content, and are typically used at very high concentrations (regularly dosed as high as 50% based on water content—glycol is often used in amounts as high as 100% of the weight of the produced water). Therefore, there is a substantial cost associated with the transportation and storage of large quantities of these solvents. A more cost-effective alternative is the use of low dosage hydrate inhibitors (LDHIs), as they generally require a dose of less than about 2% to inhibit the nucleation or growth of gas hydrates. There are two general types of LDHIs, kinetic hydrate inhibitors and anti-agglomerants which are both typically used at much lower concentrations. KHIs work by delaying the growth of gas hydrate crystals. They also function as anti-nucleators. In contrast, AAs allow hydrates to form but they prevent them from agglomerating and subsequently accumulating into larger masses capable of causing plugs. The function of an AA is to keep hydrate particles dispersed as a fluid slurry within the hydrocarbon phase.

BRIEF SUMMARY

One aspect of the invention is a hydrate inhibitor composition comprising a hydrate-inhibiting effective amount of a compound of Formula (I), or an acid, a free base, a zwitterion, or a salt thereof:

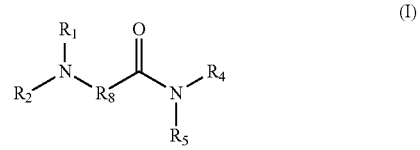

wherein $R_1$ is hydrogen, a $C_1$ to $C_{20}$ substituted or unsubstituted alkyl group, or a $C_1$ to $C_{20}$ substituted or unsubstituted alkenyl group; $R_2$ is hydrogen, a $C_1$ to $C_{20}$ substituted or unsubstituted alkyl group, or a $C_1$ to $C_{20}$ substituted or unsubstituted alkenyl group, an alkylcarboxyl, or an alkylamido group; $R_4$ and $R_5$ are independently hydrogen, a $C_1$ to $C_{20}$ substituted or unsubstituted alkyl group, a $C_1$ to $C_{20}$ substituted or unsubstituted alkenyl group, or wherein the nitrogen atom and the $R_4$ and $R_5$ groups form a substituted or unsubstituted heterocyclo group; and $R_8$ is a $C_2$ to $C_{10}$ substituted or unsubstituted alkylene group.

The present disclosure further relates to anti-agglomerant low dosage hydrate inhibitors that can inhibit the formation of hydrate agglomerants and/or plugs. Thus, a hydrate inhibitor composition can comprise at least one component selected from the group consisting of:

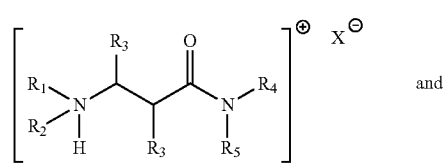 and

-continued

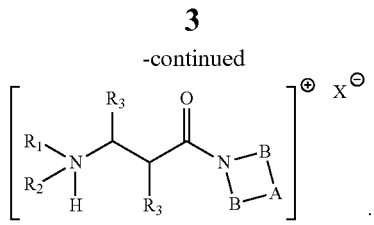

$R_1$ is an alkyl group or an alkenyl group that can contain one or more heteroatoms or ionizable heteroatoms. $R_2$ is present or not as hydrogen, depending on the ionization of the attached nitrogen atom. $R_3$ comprises a group selected from the generic formula $C_nH_{2n+1}$, wherein n is a number from 0 to 10. $R_4$ is an alkyl group or an alkenyl group that can contain one or more heteroatoms or ionizable heteroatoms. $R_5$ is selected from the group consisting of hydrogen, an alkyl group that can contain one or more heteroatoms or ionizable heteroatoms, an alkenyl group that can contain one or more heteroatoms or ionizable heteroatoms, and any combination thereof. B is a group selected from the generic formula $(CH_2)_n$, wherein n is a number from 1 to 4. A is a substituent selected from the group consisting of $CH_2$, $NR_5$, oxygen, and any combination thereof, and X is a counterion.

Another aspect is a method of inhibiting formation of hydrate agglomerants in a fluid comprising water, a gas, and optionally liquid hydrocarbon is disclosed. The method can comprise the step of adding to the fluid an effective amount of a composition comprising a hydrate inhibitor selected from the group consisting of:

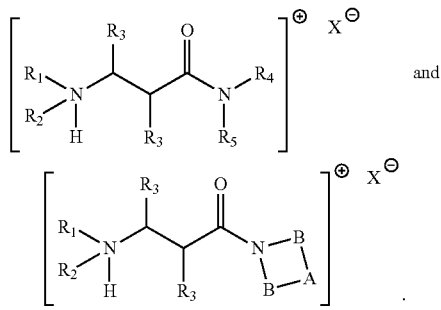

and $R_1$ is an alkyl group or an alkenyl group that can contain one or more heteroatoms or ionizable heteroatoms. $R_2$ is present or not as hydrogen, depending on the ionization of the attached nitrogen atom. $R_3$ comprises a group selected from the generic formula $C_nH_{2n+1}$, wherein n is a number from 0 to 10. $R_4$ is an alkyl group or an alkenyl group that can contain one or more heteroatoms or ionizable heteroatoms. $R_5$ is selected from the group consisting of hydrogen, an alkyl group that can contain one or more heteroatoms or ionizable heteroatoms, an alkenyl group that can contain one or more heteroatoms or ionizable heteroatoms, and any combination thereof. B is a group selected from the generic formula $(CH_2)_n$, wherein n is a number from 1 to 4. A is a substituent selected from the group consisting of $CH_2$, $NR_5$, oxygen, and any combination thereof, and X is a counterion.

The foregoing has outlined rather broadly the features and technical advantages of the present disclosure in order that the detailed description that follows can be better understood. Additional features and advantages of the disclosure will be described hereinafter that form the subject of the claims of this application. It should be appreciated by those skilled in the art that the conception and the specific embodiments disclosed can be readily utilized as a basis for modifying or designing other embodiments for carrying out the same purposes of the present disclosure. It should also be realized by those skilled in the art that such equivalent embodiments do not depart from the spirit and scope of the disclosure as set forth in the appended claims.

DETAILED DESCRIPTION

The present disclosure relates to anti-agglomerant low dosage hydrate inhibitors that can inhibit the formation of hydrate agglomerants and/or plugs. The anti-agglomerant low dosage hydrate inhibitors can be surfactants. Hereinafter, these compounds (anti-agglomerant low dosage hydrate inhibitors/surfactants) can be referred to as "hydrate inhibitors". Further, when referring to a hydrate inhibitor in the present disclosure, it is to be understood that the reference can refer to a hydrate inhibitor by itself, a combination of two or more hydrate inhibitors, or a composition comprising one or more of the inventive hydrate inhibitors disclosed herein. Also, when referring to a composition comprising a hydrate inhibitor, it is to be understood that the composition can comprise a single hydrate inhibitor or a combination of two or more of the presently disclosed hydrate inhibitors.

The hydrate inhibitors can be used for inhibiting, retarding, mitigating, reducing, controlling and/or delaying formation of hydrocarbon hydrates, agglomerants of hydrates, and/or plugs. The hydrate inhibitors can be applied to prevent, reduce, and/or mitigate plugging of conduits, pipes, transfer lines, valves, and other places or equipment where hydrocarbon hydrate solids can form.

The hydrate inhibitors can be zwitterionic compounds. These hydrate inhibitors can be used as low dosage hydrate inhibitors for inhibiting the formation or agglomeration of natural gas hydrates.

The hydrate inhibitors can be cationic ammonium surfactants. These hydrate inhibitors can be used as low dosage hydrate inhibitors for inhibiting the formation and/or agglomeration of natural gas hydrates, for example, which can lead to undesirable plugs in the petroleum industry if left untreated.

The hydrate inhibitors can also comprise an ionizable secondary amine, which is in contrast to known hydrate inhibitors, which can include tertiary, quaternary, or unionized secondary amines. A hydrate-philic group can be in close proximity to the amide linkage, which is further described and depicted below.

The presently disclosed hydrate inhibitors can be kinetic hydrate inhibitors because, in some aspects, they can act to delay hydrate formation in addition to controlling agglomeration.

Referring to the compounds of formula 1, the compounds can generally be prepared according to Schemes 1A and 1B:

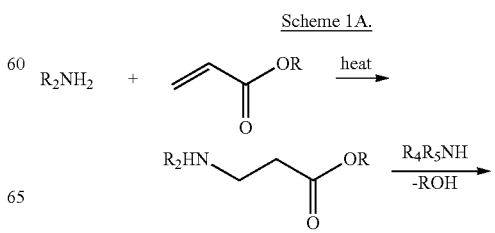

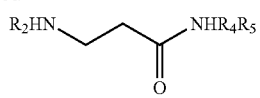

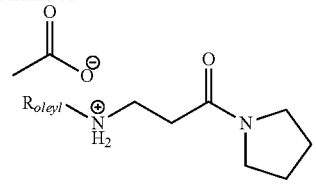

Scheme 1B.

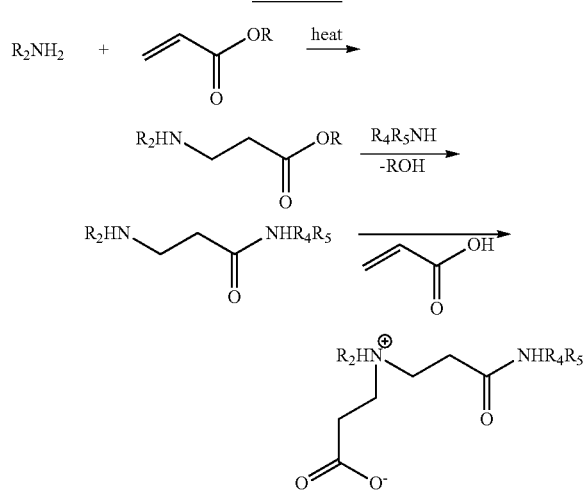

wherein $R_2$, $R_4$, and $R_5$ are as defined for the compound of formula 1 described herein. As is known to a person of ordinary skill in the art, Schemes 1A and 1B can be altered to prepare compounds having a longer carbon chain linker between the amine group and the carbonyl carbon of the amide group. The salts of these compounds can be prepared by blending the product with an acid, such as a hydrogen halide, a carboxylic acid, sulfuric acid, phosphoric acid, nitric acid, or a combination thereof.

The synthesis of specific hydrate inhibitors is detailed below. As mentioned above, the synthesis can be uniquely tailored so that the hydrate-philic group of the inhibitor is in close proximity to the amide linkage of the inhibitor. For example, oleylamine can be reacted with methyl acrylate. The reaction product can be mixed with pyrrolidine to form an amide, which can then be treated with methanol and acetic acid, for example, to form the hydrate inhibitor.

The hydrate inhibitors can be synthesized according to the following general procedures:

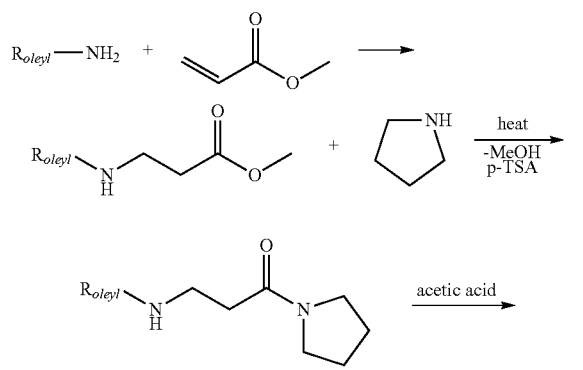

For example, the above synthesis can be carried out using the following specific reagents as illustrative examples:

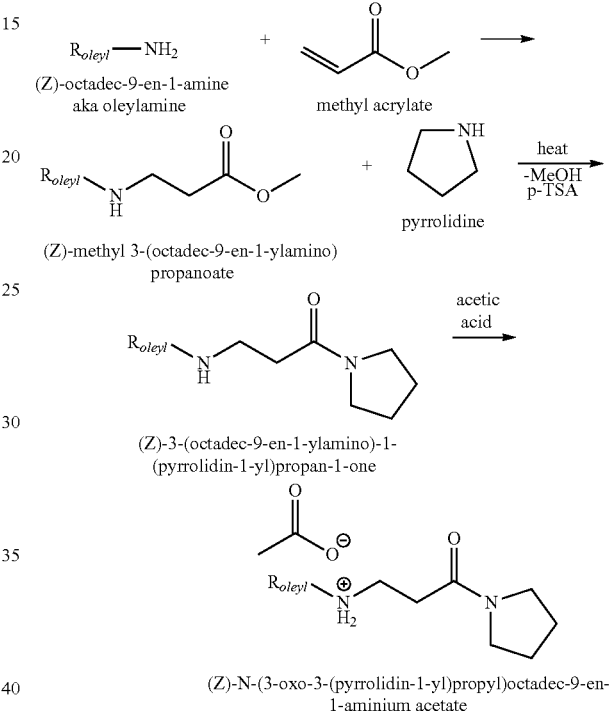

Additionally, the presently disclosed hydrate inhibitors can be synthesized according to the following procedure:

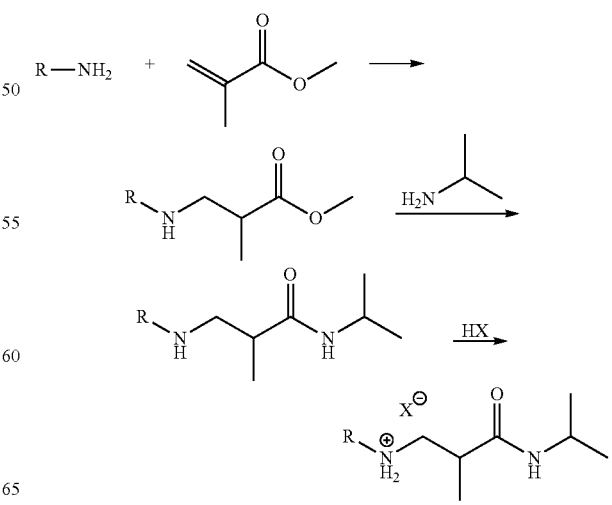

It should be noted, however, that there can be other chemical reactions that can be used to synthesize the presently disclosed hydrate inhibitors and thus, methods of making the presently disclosed hydrate inhibitors are not limited to the specific steps depicted above. All of the foregoing "R" groups are defined below in connection with the general discussion regarding the base structure of the hydrate inhibitors.

One aspect of the invention is a hydrate inhibitor composition comprising a hydrate-inhibiting effective amount of a compound of Formula (I), or an acid, a free base, a zwitterion, or a salt thereof:

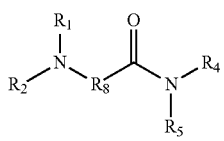

wherein $R_1$ is hydrogen, a $C_1$ to $C_{20}$ substituted or unsubstituted alkyl group, or a $C_1$ to $C_{20}$ substituted or unsubstituted alkenyl group; $R_2$ is hydrogen, a $C_1$ to $C_{20}$ substituted or unsubstituted alkyl group, or a $C_1$ to $C_{20}$ substituted or unsubstituted alkenyl group, an alkylcarboxyl, or an alkylamido group; $R_4$ and $R_5$ are independently hydrogen, a $C_1$ to $C_{20}$ substituted or unsubstituted alkyl group, a $C_1$ to $C_{20}$ substituted or unsubstituted alkenyl group, or wherein the nitrogen atom and the $R_4$ and $R_5$ groups form a substituted or unsubstituted heterocyclo group; and $R_8$ is a $C_2$ to $C_{10}$ substituted or unsubstituted alkylene group.

The substituted alkyl group of $R_1$, $R_2$, $R_4$, and $R_5$ can have at least one of the —$CH_2$— groups in the chain replaced with an ether, an amine, an amide, a carbonyl, or an ester functional group or can have at least one of the hydrogen atoms attached to a carbon atom of the chain be replaced with a hydroxy, a halo, or an amine group.

The substituted alkyl group of $R_1$, $R_2$, $R_4$, and $R_5$ can also have at least one of the —$CH_2$— groups in the chain replaced with an amine.

The compound of Formula 1 can have $R_8$ be —$C_2H_4$—.

Additionally, the compound of Formula 1 can have $R_1$ be $C_{10}$ to $C_{20}$ alkyl or —$R_{10}$—$NR_6R_7$, wherein $R_{10}$ is $C_1$ to $C_5$ alkylene, and $R_6$ and $R_7$ are independently substituted or unsubstituted $C_1$ to $C_6$ alkyl.

Further, the compound of Formula 1, $R_2$ can be —$R_{20}$—C(O)O⁻, wherein $R_{20}$ is $C_1$ to $C_4$ alkylene.

For the compound of Formula 1, $R_4$ can be hydrogen.

For the compound of Formula 1, $R_5$ can be $C_{10}$ to $C_{20}$ alkyl or —$R_{50}$—$NR_6R_7$, $R_{50}$ can $C_1$ to $C_5$ alkylene, and $R_6$ and $R_7$ can independently be $C_1$ to $C_6$ alkyl.

Additionally, the compounds of Formula 1 can have $R_{20}$ be —$C_2H_4$—, and $R_{50}$ be —$C_3H_6$—.

The compound of Formula 1 can have the following structures:

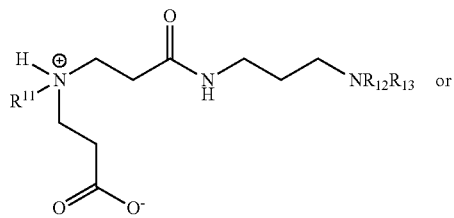

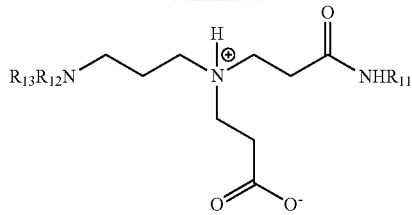

wherein $R_{11}$ is $C_8$ to $C_{20}$ alkyl, and $R_{12}$ and $R_{13}$ are independently $C_1$ to $C_6$ alkyl.

Preferably, $R_{11}$ is $C_{12}$ to $C_{20}$ unsubstituted alkyl, and $R_{12}$ and $R_{13}$ are independently $C_1$ to $C_4$ unsubstituted alkyl.

Additionally, the compound of Formula 1 can be:

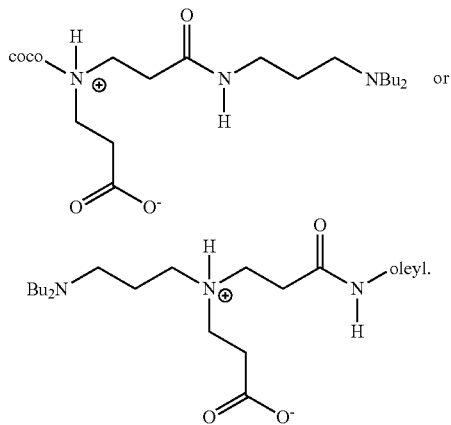

When the compound of Formula 1 is in its salt form, the counterion can be selected from the group consisting of a halide, a carboxylate, hydrogen sulfate, dihydrogen phosphate, nitrate, and a combination thereof. Preferably, the counterion can be an acetate, an acrylate, or a combination thereof.

The hydrate inhibitor can comprise one of the following cationic generic chemical structures:

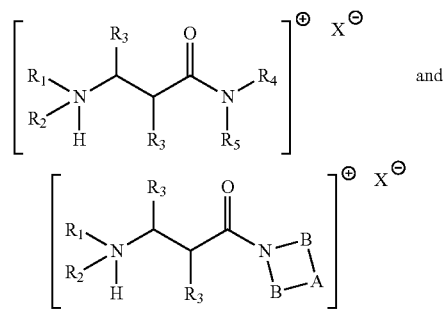

$R_1$ can be any alkyl or alkenyl group that can contain one or more heteroatoms or ionizable heteroatoms. $R_1$ can comprise any group having from about 8 carbons atoms to about 20 carbon atoms, e.g. a $C_8$ to $C_{20}$ group. For example, $R_1$ can comprise a $C_8$ to $C_{12}$ group, a $C_{12}$ to $C_{16}$ group, or a $C_{16}$ to $C_{20}$ group. Preferably, $R_1$ can comprise a $C_8$ group, a $C_{10}$ group, a $C_{18}$ group, or a $C_{20}$ group.

For these cationic structures, $R_2$ can comprise hydrogen (H) or no atom or group at all, depending upon ionization of the attached nitrogen atom.

These cationic structures can have $R_3$ comprise a group selected from the generic formula $C_nH_{2n+1}$, wherein "n" is a number from 0 to 10. For these compounds, "n" can be 0 or 1.

The cationic structures can have $R_4$ be any alkyl or alkenyl group that can contain one or more heteroatoms or ionizable heteroatoms and $R_5$ can be H, any alkyl group that can contain one or more heteroatoms or ionizable heteroatoms, or any alkenyl group that can contain one or more heteroatoms or ionizable heteroatoms. B comprises a group selected from the generic formula $(CH_2)_n$, wherein "n" is a number from 1 to 4. A comprises a substituent selected from $CH_2$, $NR_5$, or oxygen (O) and X can comprise any counterion, such as a halide, any carboxylate, hydrogen sulfate, dihydrogen phosphate, or nitrate. Non-limiting examples include acetate and acrylate.

For these cationic structures, the term "alkenyl" refers to a monovalent group derived from a straight, branched, or cyclic hydrocarbon containing at least one carbon-carbon double bond by the removal of a single hydrogen atom from each of two adjacent carbon atoms of an alkyl group. Representative alkenyl groups include, for example, ethenyl, propenyl, oleyl, butenyl, 1-methyl-2-buten-1-yl, and the like.

For these cationic structures, the term "alkyl" refers to a monovalent group derived by the removal of a single hydrogen atom from a straight or branched chain or cyclic saturated or unsaturated hydrocarbon. Representative alkyl groups include methyl, ethyl, propyl, butyl, pentyl, hexyl, heptyl, octyl, nonyl, decyl, lauryl, and the like.

Further to the cationic generic structures depicted in the foregoing paragraph, the following are additional compositions that have been synthesized and are intended to be covered under the scope of the presently disclosed hydrate inhibitors:

substituent is located at either of the "B" group positions and the "B2" substituent is located at either of the "B" group positions.

Specifically, the hydrate inhibitor comprises the following general structure:

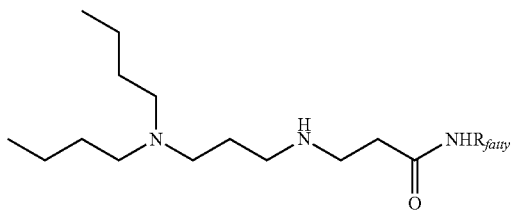

wherein "$R_{fatty}$" is any alkyl group having from about 8 carbon atoms to about 20 carbon atoms, e.g. a $C_8$ to $C_{20}$ group. For example, $R_{fatty}$ can comprise a $C_8$ to $C_{12}$ group, a $C_{12}$ to $C_{16}$ group, or a $C_{16}$ to $C_{20}$ group. For this structure, $R_{fatty}$ comprises a $C_8$ group, a $C_{10}$ group, a $C_{12}$ group, a $C_{18}$ group, or a $C_{20}$ group.

Further, the hydrate inhibitor comprises the following general structure:

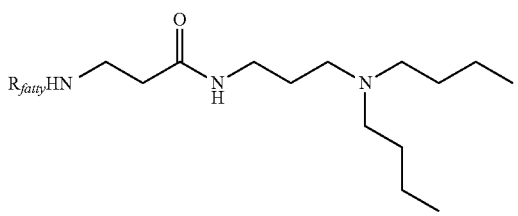

TABLE 1

| Example | R1 | R2 | R4 | R5 | B1 | B2 | X |
|---|---|---|---|---|---|---|---|
| 1 | oleyl | H | — | — | C2H4 | CH2 | acetate |
| 2 | oleyl | H | — | — | C2H4 | CH2 | sulfate |
| 3 | coco | H | — | — | C2H4 | CH2 | acrylate |
| 4 | coco | H | C3H6(N(C2H4C(CH3)2)2) | H | — | — | 2 × acetate |
| 5 | coco | — | C3H6(N(C2H4C(CH3)2)2) | H | — | — | acetate |
| 6 | oleyl | H | C3H6(N(C2H4C(CH3)2)2) | H | — | — | 2 × acetate |
| 7 | oleyl | H | C3H6(N(C4H9)2)) | H | — | — | 2 × acetate |
| 8 | coco | — | C3H6(N(C4H9)2)) | H | — | — | acrylate |
| 9 | oleyl | H | — | — | C2H4 | C3H6 | acetate |
| 10 | oleyl | H | — | — | C2H4 | C3H6 | acrylate |
| 11 | coco | H | — | — | C2H4 | C3H6 | sulfate |
| 12 | coco | H | C4H9 | C4H9 | — | — | acrylate |
| 13 | C3H6(N(C2H4C(CH3)2)2) | H | oleyl | H | — | — | 2 × acetate |
| 14 | C3H6(N(C2H4C(CH3)2)2) | — | coco | H | — | — | acrylate |
| 15 | C3H6(N(C4H9)2)) | H | oleyl | H | — | — | 2 × acetate |
| 16 | C3H6(N(C4H9)2)) | H | coco | H | — | — | 2 × acetate |

In connection with the specific compounds listed in the foregoing Table 1 and the generic structures depicted above, $R_3$ was selected to be hydrogen and "A" was selected to be $CH_2$. Although the generic structure above only lists "B" as two of the substituents and Table 1 lists "B1" and "B2", the generic structure is intended to cover wherein the "B1"

wherein "$R_{fatty}$" is any alkyl group having from about 8 carbons atoms to about 20 carbon atoms, e.g. a $C_8$ to $C_{20}$ group. For example, $R_{fatty}$ can comprise a $C_8$ to $C_{12}$ group, a $C_{12}$ to $C_{16}$ group, or a $C_{16}$ to $C_{20}$ group. Further, $R_{fatty}$ comprises a $C_8$ group, a $C_{10}$ group, a $C_{18}$ group, or a $C_{20}$ group.

With respect to the term "hydrate-philic" used in the present disclosure when describing a certain portion of the hydrate inhibitor molecule, the portion of the molecule being referred to as the hydrate-philic portion is, with respect to the specific composition shown above, the portion opposite the $R_{fatty}$ group. That is, in the above example, the portion including the tertiary N atom and the two butyl groups.

Particularly, the hydrate inhibitor comprises the following general structure:

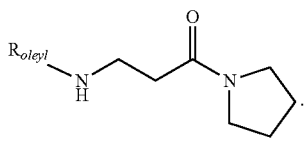

With respect to the prior art anti-agglomerant inhibitors, the hydrate-philic portion of the inhibitor molecule is also the portion of the molecule comprising the charge and the amide comprised the fatty tail, which was considered necessary for anti-agglomerant functionality. However, the present inventors have discovered a highly functional hydrate inhibitor comprising the fatty tail on the non-traditional side of the molecule (the side opposite of the amide, wherein the amide does not comprise the fatty tail) instead forming a secondary amine that can also serve as the site for salting. In the prior art, the positive charge has always centered around a quaternary or tertiary amine but not a secondary amine as in the presently disclosed hydrate inhibitors.

The compositions disclosed herein, which comprise one or more hydrate inhibitors, can further comprise one or more additional chemistries. The composition can further comprise at least one additional hydrate inhibitor. Exemplary additional hydrate inhibitors are disclosed in U.S. patent application Ser. No. 12/253,504, filed Oct. 17, 2008, Ser. No. 12/253,529, filed Oct. 17, 2008, Ser. No. 12/400,428, filed Mar. 9, 2009, and Ser. No. 12/967,811, filed Dec. 16, 2008, the disclosures of which are incorporated into the present application in their entireties.

The composition comprising the hydrate inhibitor can further comprise one or more thermodynamic hydrate inhibitors, one or more kinetic hydrate inhibitors, one or more anti-agglomerants, or any combination thereof.

The composition can also further comprise one or more asphaltene inhibitors, paraffin inhibitors, corrosion inhibitors, scale inhibitors, emulsifiers, water clarifiers, dispersants, emulsion breakers, or any combination thereof.

Additionally, the composition can further comprise one or more polar or nonpolar solvents or a mixture thereof. Preferably, the composition further comprises one or more solvents selected from the group consisting of isopropanol, methanol, ethanol, 2-ethylhexanol, heavy aromatic naphtha, toluene, ethylene glycol, ethylene glycol monobutyl ether (EGMBE), diethylene glycol monoethyl ether, xylene, or any combination thereof.

The composition comprising the hydrate inhibitor can be introduced into the fluid by any means suitable for ensuring dispersal of the hydrate inhibitor through the fluid being treated. Typically, the composition comprising the hydrate inhibitor is injected using mechanical equipment such as chemical injection pumps, piping tees, injection fittings, and the like. The composition comprising the hydrate inhibitor can be injected as prepared or formulated in one or more additional polar or non-polar solvents, depending upon the application and requirements.

Representative polar solvents suitable for formulation with the hydrate inhibitor composition include water, brine, seawater, alcohols (including straight chain or branched aliphatic such as methanol, ethanol, propanol, isopropanol, butanol, 2-ethylhexanol, hexanol, octanol, decanol, 2-butoxyethanol, etc.), glycols and derivatives (ethylene glycol, 1,2-propylene glycol, 1,3-propylene glycol, ethylene glycol monobutyl ether, etc.), ketones (cyclohexanone, diisobutylketone), N-methylpyrrolidinone (NMP), N,N-dimethylformamide, and the like.

Representative non-polar solvents suitable for formulation with the hydrate inhibitor composition include aliphatics, such as pentane, hexane, cyclohexane, methylcyclohexane, heptane, decane, dodecane, diesel, and the like, and aromatics, such as toluene, xylene, heavy aromatic naphtha, fatty acid derivatives (acids, esters, amides), and the like.

The composition comprising the hydrate inhibitor can be used in a method of inhibiting the formation of hydrate agglomerants in an aqueous medium comprising water, gas, and optionally liquid hydrocarbon. The method comprises adding to the aqueous medium an effective amount of a composition comprising one or more hydrate inhibitors.

The compositions and methods of this disclosure are effective to control gas hydrate formation and plugging during hydrocarbon production and transportation. Specifically, the hydrate inhibitor can be injected prior to substantial formation of hydrates. An exemplary injection point for petroleum production operations is downhole near the surface controlled sub-sea safety valve. This ensures that during a shut-in, the product is able to disperse throughout the area where hydrates will occur. Treatment can also occur at other areas in the flowline, taking into account the density of the injected fluid. If the injection point is well above the hydrate formation depth, then the hydrate inhibitor can be formulated with a solvent having a density high enough that the inhibitor will sink in the flowline to collect at the water/oil interface. Moreover, the treatment can also be used in pipelines or anywhere in the system where the potential for hydrate formation exists.

Further, the composition comprising the hydrate inhibitor can be applied to an aqueous medium that contains various levels of salinity. The fluid can have a salinity of about 0% to about 25% or about 10% to about 25% weight/weight (w/w) total dissolved solids (TDS). The aqueous medium in which the disclosed compositions are applied can be contained in many different types of apparatuses, especially those that transport an aqueous medium from one location to another.

The aqueous medium can be contained in an oil and gas pipeline. Additionally, the aqueous medium can be contained in refineries, such as separation vessels, dehydration units, gas lines, and pipelines.

Further, the presently disclosed hydrate inhibitors can function as corrosion inhibitors useful to inhibit the corrosion of any surface that they can contact, such as the surfaces found in refineries, such as separation vessels, dehydration units, gas lines, and pipelines.

The hydrate inhibitors can also display antimicrobial properties in refineries, such as separation vessels, dehydration units, gas lines, and pipelines.

The composition comprising the hydrate inhibitor can be applied to an aqueous medium that contains various levels of water cut. One of ordinary skill in the art understands that "water cut" refers to the % of water in a composition containing an oil and water mixture. In particular, the water cut of the aqueous medium can be from about 1% to about 80% w/w based on the total weight of the aqueous medium comprising water, gas, and optionally liquid hydrocarbon.

The compositions of the present disclosure can be applied to an aqueous medium using various well-known methods and they can be applied at numerous different locations throughout a given system. The composition comprising the hydrate inhibitor can be pumped into an oil/gas pipeline using an umbilical line. Further, capillary string injection systems can be utilized to deliver the composition. U.S. Pat. No. 7,311,144 provides a description of an apparatus and methods relating to capillary injection, the disclosure of which is incorporated into the present application in its entirety.

Various dosage amounts of the composition and/or the hydrate inhibitor(s) can be applied to the aqueous medium to inhibit the formation of hydrate agglomerants. One of ordinary skill in the art is able to calculate the amount of hydrate inhibitor or composition comprising a hydrate inhibitor for a given situation without undue experimentation. Factors that would be considered of importance in such calculations include, for example, content of aqueous medium, percentage water cut, API gravity of hydrocarbon, and test gas composition. Further, the hydrate inhibitor(s) is added in an amount from about 0.1 to about 5 volume %, based on water cut.

A method of inhibiting formulation of hydrate agglomerants in a fluid comprising water, a gas, and optionally a liquid hydrocarbon, comprising contacting the fluid with an effective amount of a hydrate inhibitor composition as described herein.

The fluid can be contained in an oil pipeline, a gas pipeline, or a refinery.

The composition can be added downhole near a surface controlled sub-sea safety value.

When the nitrogen atom and $R_4$ and $R_5$ form a heterocyclo group, the group can be considered a "nitrogen-containing heterocycle" that can denote optionally substituted, fully saturated or unsaturated, monocyclic or bicyclic, aromatic or nonaromatic groups having at least one nitrogen atom in at least one ring, and preferably 5 or 6 atoms in each ring. The nitrogen-containing heterocycle can also contain 1 or 2 oxygen atoms or 1 or 2 sulfur atoms in the ring. Exemplary nitrogen-containing heterocycles include pyrrole, pyrroline, pyrrolidine, piperidine, pyrazole, pyrazoline, pyrazolidine, imidazole, imidazoline, imidazolidine, triazole, isoxazole, isoxazoline, isoxazolidine, oxazole, oxazoline, oxazolidine, thiazole, isothiazole, oxadiazole, oxatriazole, dioxazole, oxathiazole, pyridine, pyridazine, pyrimidine, pyrazine, piperazine, triazine, oxazine, oxathiazine, oxazine, isoxazine, oxadiazine, morpholine, azepane, azepine, caprolactam, or quinoline. When substituted, exemplary substituents include one or more of the following groups: substituted or unsubstituted alkyl, substituted or unsubstituted alkenyl, substituted or unsubstituted alkynyl, substituted or unsubstituted aryl, substituted or unsubstituted aralkyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

Unless otherwise indicated, an alkyl group as described herein alone or as part of another group is an optionally substituted linear saturated monovalent hydrocarbon substituent containing from one to thirty carbon atoms in the main chain, or an optionally substituted branched saturated monovalent hydrocarbon substituent containing three to sixty carbon atoms, and preferably one to twenty carbon atoms in the main chain. Examples of unsubstituted alkyl groups include methyl, ethyl, n-propyl, i-propyl, n-butyl, i-butyl, s-butyl, t-butyl, n-pentyl, i-pentyl, s-pentyl, t-pentyl, and the like.

Unless otherwise indicated, the alkenyl groups described herein are preferably lower alkenyl containing from two to thirty carbon atoms in the principal chain and up to 60 carbon atoms. They can be straight or branched chain or cyclic and include ethenyl, propenyl, isopropenyl, butenyl, isobutenyl, hexenyl, and the like.

The terms "aryl" or "ar" as used herein alone or as part of another group (e.g., aralkyl) denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl. The term "aryl" also includes heteroaryl.

The term "-ene" as used as a suffix as part of another group denotes a bivalent substituent in which a hydrogen atom is removed from each of two terminal carbons of the group, or if the group is cyclic, from each of two different carbon atoms in the ring. For example, alkylene denotes a bivalent alkyl group such as methylene (—$CH_2$—) or ethylene (—$CH_2CH_2$—), and arylene denotes a bivalent aryl group such as o-phenylene, m-phenylene, or p-phenylene.

The term "substituted" as in "substituted aryl," "substituted alkyl," and the like, means that in the group in question (i.e., the alkyl, aryl or other group that follows the term), at least one hydrogen atom bound to a carbon atom is replaced with one or more substituent groups such as hydroxy (—OH), alkylthio, phosphino, amido (—CON($R_A$)($R_B$), wherein $R_A$ and $R_B$ are independently hydrogen, alkyl, or aryl), amino(—N($R_A$)($R_B$), wherein $R_A$ and $R_B$ are independently hydrogen, alkyl, or aryl), halo (fluoro, chloro, bromo, or iodo), silyl, nitro (—$NO_2$), an ether (—$OR_A$ wherein $R_A$ is alkyl or aryl), an ester (—OC(O)$R_A$ wherein $R_A$ is alkyl or aryl), keto (—C(O)$R_A$ wherein $R_A$ is alkyl or aryl), heterocyclo, and the like. Further, an alkylene group in the chain can be replaced with an ether, an amine, an amide, a carbonyl, an ester, a cycloalkyl, or a heterocyclo functional group. When the term "substituted" introduces a list of possible substituted groups, it is intended that the term apply to every member of that group. That is, the phrase "optionally substituted alkyl or aryl" is to be interpreted as "optionally substituted alkyl or optionally substituted aryl."

"Arylalkyl" means an aryl group attached to the parent molecule through an alkylene group. The number of carbon atoms in the aryl group and the alkylene group is selected such that there is a total of about 6 to about 18 carbon atoms in the arylalkyl group. A preferred arylalkyl group is benzyl.

"Inhibiting" includes both inhibiting and preventing the formation and agglomeration of hydrate crystals.

Unless otherwise indicated herein, "AA" means anti-agglomerant; "IPA" means isopropanol (isopropyl alcohol); "KHI" means kinetic hydrate inhibitor; "LDHI" means low-dosage hydrate inhibitor; "MeOH" means methanol; "NaCl" means sodium chloride; "PE" means pentaerythritol; and "THI" means thermodynamic hydrate inhibitor.

EXAMPLES

To evaluate the performance of the presently disclosed hydrate inhibitors and prove their superior properties as hydrate inhibitors, a rocking cell test was used. The rocking cell test is a commonly used test in the art for assessing the performance of anti-agglomerant chemistry. Briefly, chemistries are evaluated based on their ability to effectively minimize the size of hydrate agglomerant particles and then disperse those particles into the hydrocarbon phase. Chemical performance is evaluated by determining the minimum effective dose (MED) required to register as a "pass" in the rocking cell test.

The rocking cell generally includes individual cells and a rack on which the cells are placed. The cells can comprise sapphire tubing containing a stainless steel ball and can withstand pressures up to about 5,000 psi. Once the cells are mounted onto the rack, the rack rocks up and down slowly, at a rate of about 1 complete cycle (up and down) per minute. The rack is further contained within a temperature controlled bath attached to a chiller.

Anti-agglomerant test cells generally contain three components: hydrocarbon, aqueous phase, and gas. In these examples, the inventors injected a synthetic brine of about 10.3% salinity into each cell followed by a particular does of hydrate inhibitor. In the experiments the hydrate inhibitor was dosed according to the amount of aqueous phase in the test cell. The last component added to each cell was warm crude oil. The initial temperature of the test was about 80° F., and at that temperature, the cells are charged with a synthetic natural gas (SNG) mixture to about 2,500 psi. The test is a constant pressure test where the cells are left open to a booster that boosts additional gas into the cells as gas is solubilized into the fluids and/or forms hydrates. The cells were rocked for about 0.5 hours to equilibrate and mix prior to stopping at a horizontal position and cooling down to about 40° F. over an 8 hour period of time. After a shut-in time of about 48 hours at temperature, the cells were rocked again for an hour, and visual observations were recorded. Table 2 below shows the results from some of the rocking cell tests.

Examples 1, 2, 16, 4, and 8 correspond to Examples 1, 2, 16, 4, and 8 in Table 1. The comparative examples were as follows:

TABLE 2

| Example | Minimum Effective Dose Rate (vol %) |
|---|---|
| Comparative Example A | 5.0 |
| Comparative Example B | 3.5 |
| 1 | 2.0 |
| 2 | 1.5 |
| 16 | 1.5 |

TABLE 2-continued

| Example | Minimum Effective Dose Rate (vol %) |
|---|---|
| 4 | 1.0 |
| 8 | 0.75 |

The presently disclosed hydrate inhibitors can be synthesized according to any methods known in the art. As an illustrative example, the hydrate inhibitors can be synthesized as follows:

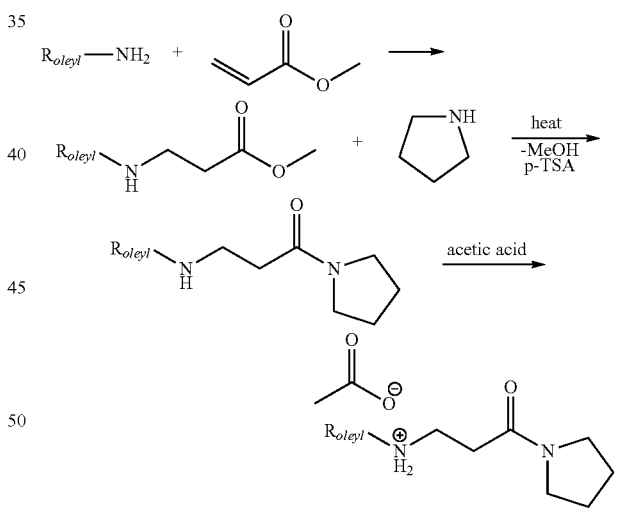

To a 500-mL, 3-neck round bottom flask was added about 100.0 g (0.374 mol) oleylamine and a magnetic stir bar. The flask was fitted with a thermocouple, reflux condenser, and addition funnel containing about 32.18 g (0.374 mol) methyl acrylate. The acrylate was added to the stirring amine slowly. Once the addition was complete, the mixture was stirred for about 1 hour. LC-MS and FT-IR confirmed full conversion of the starting materials.

To the resulting yellow liquid was added about 26.59 g (0.374 mol) pyrrolidine and catalytic para-toluenesulfonic acid (about 0.79 g). An insulated Dean-Stark apparatus was attached between the round bottom flask and reflux condenser for methanol removal. The reaction mixture was heated to about 90° C. for about 12 hours, at which time FT-IR analysis confirmed the disappearance of the ester. Upon cooling to ambient temperature, a yellow-orange liquid was formed. To the resulting amide at ambient temperature was added about 97.39 g methanol and then about 19.36 g (0.322 mol) of acetic acid, and the mixture was stirred at ambient temperature for about 2 hours to produce the hydrate inhibitor.

As an illustrative example, the zwitterionic hydrate inhibitors can be synthesized as follows:

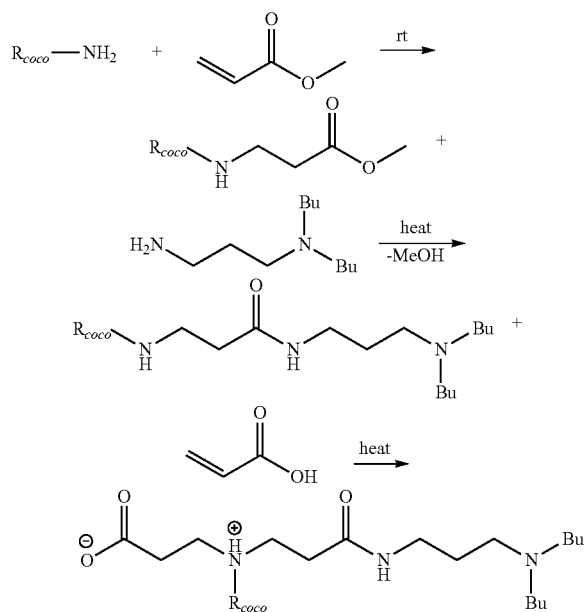

To a 500-mL, 3-neck round bottom flask, was added about 100.0 g (0.523 mol) cocoamine and a magnetic stir bar. The flask was fitted with a thermocouple, reflux condenser, and an addition funnel containing about 45.06 g (0.523 mol) methyl acrylate. The acrylate was slowly added to the stirring amine at room temperature. Once the addition was complete, the mixture was stirred for about 1 hour. LC-MS and FT-IR confirmed full converted of the starting materials.

To the resulting yellow liquid, was added about 97.53 g (0.523 mol) dibutylaminopropylamine. An insulated Dean-Stark apparatus was attached between the round bottom flask and reflux condenser for removal of the methanol. The reaction mixture was heated to 165° C. for about 6 hours, at which time FT-IR analysis confirmed the disappearance of the ester. Upon cooling to ambient temperature, an off-white solid was formed. After melting the off-white amide solid at 40° C. in a water bath, about 100.0 g (0.232 mol) was charged to a 500-mL, 3-neck round bottom flask was equipped with an overhead stirred with a stir blade, thermocouple, and an addition funnel contained about 16.72 g of acrylic acid. The acrylic acid was slowly added to the stirring amide at room temperature, and then heated to 90° C. for about 6 hours to yield the Michael addition product, a syrupy orange liquid. After cooling room temperature, about 25.0 g (0.050 mol) of the resulting betaine product was combined with about 23.87 g of methanol to form a homogeneous liquid solution.

To evaluate the performance of the presently disclosed hydrate inhibitors and their properties as hydrate inhibitors, a rocking cell test was used. The rocking cell test is a commonly used test in the art for assessing the performance of anti-agglomerant chemistry. Briefly, chemistries are evaluated based on their ability to effectively minimize the size of hydrate agglomerant particles and then disperse those particles into the hydrocarbon phase. Chemical performance is evaluated by determining the minimum effective dose (MED) required to register as a "pass" in the rocking cell test.

The rocking cell generally includes individual cells and a rack on which the cells are placed. The cells can comprise sapphire tubing containing a stainless steel ball and can withstand pressures up to about 5,000 psi. Once the cells are mounted onto the rack, the rack rocks up and down slowly, at a rate of about 1 complete cycle (up and down) per minute. The rack is further contained within a temperature controlled bath attached to a chiller.

Anti-agglomerant test cells generally contain three components: a hydrocarbon, an aqueous phase, and a gas. In these examples, the inventors injected a synthetic brine of about 10.3% salinity into each cell followed by a particular dose of hydrate inhibitor. In the experiments, the hydrate inhibitor was dosed according to the amount of aqueous phase in the test cell. The last component added to each cell was warm crude oil from various oil fields designated as Oil A-E. The initial temperature of the test was about 80° F. (26° C.), and at that temperature, the cells are charged with a synthetic natural gas (SNG) mixture to about 2,500 psi. The test is a constant pressure test where the cells are left open to a booster that boosts additional gas into the cells as gas is solubilized into the fluids and/or forms hydrates. The cells were rocked for about 0.5 hours to equilibrate and mix prior to stopping at a horizontal position and cooling down to about 40° F. over an 8 hour period of time. After a shut-in time of about 48 hours at temperature, the cells were rocked again for 1 hour, and visual observations were recorded. Tests performed using Oil D where run in an autoclave.

The hydrate inhibitor of Example 17 had the structure of:

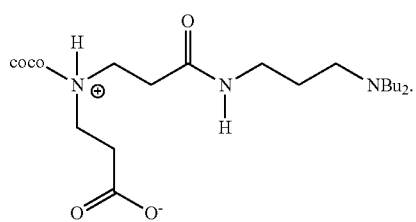

The hydrate inhibitor of Example 18 had the structure of:

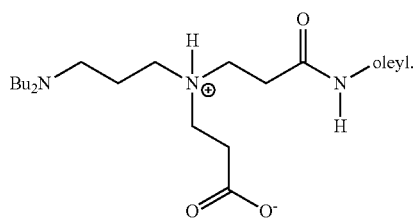

Traditionally used anti-agglomerants were used to compare the performance of the compounds described herein. The comparative anti-agglomerants used were commercial products designated as C, D, E, and F.

Table 3 below shows the results from some of the rocking cell tests.

TABLE 3

| Example | Oil A (50% w/c) | Oil B (15% w/c) | Oil C (30% w/c) | Oil D (60% w/c) | Oil E (50% w/c) |
|---|---|---|---|---|---|
| | Minimum Effective Dose (MED) (vol. %) | | | | |
| 17 | >6.0 | 3.5 | 3.0 | 1.5 | >4.0 |
| 18 | — | — | — | — | 2.0 |
| C | >2.0 | >5.0 | 2.0 | 3.0 | — |
| D | 5.0 | >5.0 | >3.0 | >6.0 | — |
| E | 0.5 | >5.0 | 2.5 | 1.5 | >5.0 |
| F | 6.0 | >5.0 | 2.0 | — | — |

All of the compositions and methods disclosed and claimed herein can be made and executed without undue experimentation in light of the present disclosure. While this invention can be embodied in many different forms, there are described in detail herein specific preferred embodiments of the invention. The present disclosure is an exemplification of the principles of the invention and is not intended to limit the invention to the particular embodiments illustrated. In addition, unless expressly stated to the contrary, use of the term "a" is intended to include "at least one" or "one or more." For example, "a device" is intended to include "at least one device" or "one or more devices."

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various compositions and methods described herein. It should also be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

What is claimed is:

1. A hydrate inhibitor composition comprising a hydrate-inhibiting effective amount of a compound of Formula (I), or an acid, a free base, a zwitterion, or a salt thereof:

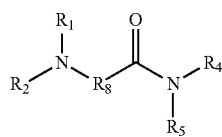

(I)

wherein
$R_1$ is hydrogen, a $C_1$ to $C_{20}$ substituted or unsubstituted alkyl group, or a $C_1$ to $C_{20}$ substituted or unsubstituted alkenyl group;
$R_2$ is an alkylcarboxyl, or an alkylamido group;
$R_4$ is hydrogen, a $C_1$ to $C_{20}$ substituted or unsubstituted alkyl group, or a $C_1$ to $C_{20}$ substituted or unsubstituted alkenyl group;
$R_5$ is $C_{10}$ to $C_{20}$ alkyl or —$R_{50}$—$NR_6R_7$, wherein $R_{50}$ is $C_1$ to $C_5$ alkylene, and $R_6$ and $R_7$ are independently $C_1$ to $C_6$ alkyl; and
$R_8$ is a $C_2$ to $C_{10}$ substituted or unsubstituted alkylene group.

2. The composition of claim 1, wherein the substituted alkyl group of $R_1$ and $R_4$ has at least one of the —$CH_2$— groups in the chain replaced with an ether, an amine, an amide, a carbonyl, or an ester functional group or at least one of the hydrogen atoms attached to a carbon atom of the chain is replaced with a hydroxy, a halo, or an amine group.

3. The composition of claim 2, wherein the substituted alkyl group of $R_1$ and $R_4$ has at least one of the —$CH_2$— groups in the chain replaced with an amine.

4. The composition of claim 1, wherein $R_8$ is —$C_2H_4$—.

5. The composition of claim 4, wherein $R_1$ is $C_{10}$ to $C_{20}$ alkyl or —$R_{10}$—$NR_6R_7$, wherein $R_{10}$ is $C_1$ to $C_5$ alkylene, and $R_6$ and $R_7$ are independently substituted or unsubstituted $C_1$ to $C_6$ alkyl.

6. The composition of claim 1, wherein $R_2$ is —$R_{20}$—C(O)O$^-$, wherein $R_{20}$ is $C_1$ to $C_4$ alkylene.

7. The composition of claim 1, wherein $R_4$ is hydrogen.

8. The composition of claim 6, wherein $R_{20}$ is $C_2H_4$, and $R_{50}$ is $C_3H_6$.

9. The composition of claim 1, wherein when the compound is in its salt form, the counterion is selected from the group consisting of a halide, a carboxylate, hydrogen sulfate, dihydrogen phosphate, nitrate, and a combination thereof.

10. The composition of claim 9, wherein the counterion is an acetate, an acrylate, or a combination thereof.

11. The composition of claim 1, wherein the composition further comprises a thermodynamic hydrate inhibitor, a kinetic hydrate inhibitor, an anti-agglomerant, or a combination thereof.

12. The composition of claim 1, wherein the composition further comprises a polar solvent, a nonpolar solvent, or a mixture thereof.

13. A method of inhibiting formation of hydrate agglomerants in a fluid comprising water, a gas, and optionally a liquid hydrocarbon, comprising contacting the fluid with an effective amount of a hydrate inhibitor composition of claim 1.

14. The method of claim 13, wherein the effective amount is from about 0.1 to about 10 volume %, based on an amount of water.

15. A hydrate inhibitor composition comprising a hydrate-inhibiting effective amount of:

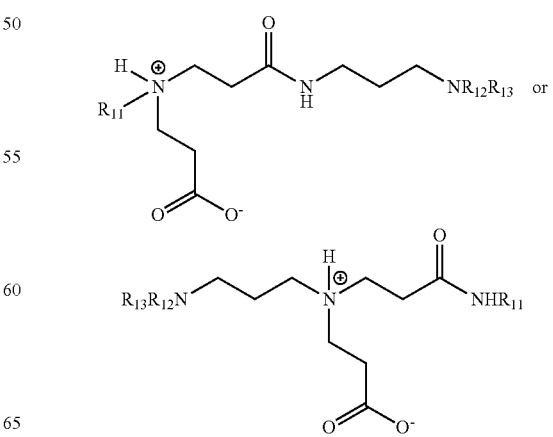

wherein $R_{11}$ is $C_8$ to $C_{20}$ alkyl, and $R_{12}$ and $R_{13}$ are independently $C_1$ to $C_6$ alkyl.
16. The composition of claim 15 wherein the compound of Formula 1 is:
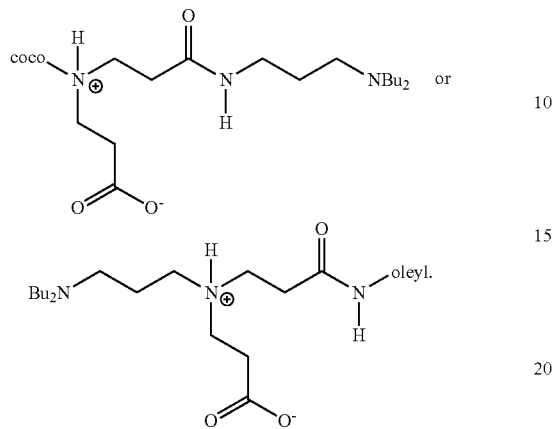
* * * * *